United States Patent
Gschweitl

Patent Number: 5,456,127
Date of Patent: Oct. 10, 1995

[54] METHOD FOR DETERMINING THE PURITY OF TREATED USED GLASS PRIOR TO RECYCLING

[75] Inventor: Karlheinz Gschweitl, Grospesendorf, Austria

[73] Assignee: Binder + Co Aktiengesellschaft, Gleisdorf, Austria

[21] Appl. No.: 195,629

[22] Filed: Feb. 14, 1994

[30] Foreign Application Priority Data

Mar. 15, 1993 [AT] Austria .................. 506/93

[51] Int. Cl.$^6$ .................. G01N 33/38; B07C 5/10
[52] U.S. Cl. .................. 73/866; 209/588; 209/587
[58] Field of Search .................. 73/866; 209/587, 209/588

[56] References Cited

U.S. PATENT DOCUMENTS

| | | | |
|---|---|---|---|
| 3,650,396 | 3/1972 | Gillespie et al. | 209/930 |
| 3,802,558 | 4/1974 | Rhys | 209/588 |
| 3,897,330 | 7/1975 | Rhys | 209/930 |
| 4,031,004 | 6/1977 | Sommer, Jr. et al. | 209/212 |
| 4,407,415 | 10/1983 | Böhme et al. | 209/556 |
| 4,513,868 | 4/1985 | Culling et al. | 209/587 |
| 4,572,666 | 2/1986 | Satake | 207/588 |
| 4,657,144 | 4/1987 | Martin et al. | 209/587 |
| 4,787,495 | 11/1988 | Tuten et al. | 209/930 |
| 5,314,071 | 5/1994 | Christian et al. | 209/587 |
| 5,321,496 | 6/1994 | Shofner et al. | 356/238 |

FOREIGN PATENT DOCUMENTS

| | | |
|---|---|---|
| 0353457 | 2/1990 | European Pat. Off. . |
| 3002239 | 7/1981 | Germany . |
| 986177 | 3/1965 | United Kingdom ............ 209/588 |
| 501 | 1/1988 | WIPO ............................ 209/588 |

*Primary Examiner*—Hezron E. Williams
*Assistant Examiner*—Daniel S. Larkin
*Attorney, Agent, or Firm*—Collard & Roe

[57] ABSTRACT

A method for determining the purity of treated used glass, in which the sample quantity is taken from the treated used glass stream and the foreign bodies still contained therein, separated according to non-ferrous metals and opaque foreign materials such as ceramic and porcelain particles and stones, are sorted out, weighed and put in relation to the weight of the whole sample. In order to be able to analyze a sample in a simple manner, it is provided that the sample is piled in one layer and allowed to trickle over a free-falling path and that foreign bodies made from non-ferrous metals are blown out and thereafter opaque foreign bodies are blown out and collected in containers separate from the non-ferrous metals.

1 Claim, 2 Drawing Sheets

METHOD FOR DETERMINING THE PURITY OF TREATED USED GLASS PRIOR TO RECYCLING

BACKGROUND OF THE INVENTION

1. Field of the Invention

The invention relates to a method for determining the purity of treated used glass prior to recycling for determining the purity of the treated used glass, in which a sample quantity is removed from a stream of treated used glass and any foreign bodies still contained therein are separated into sorted fractions respectively comprised of non-ferrous metals and opaque foreign materials such as ceramic and porcelain particles and stones, the sorted fractions are weighed and the weight of the sorted fractions is related to the weight of the whole sample quantity.

2. Description of the Prior Art

The treatment of used glass must ensure a high degree of freedom from foreign materials. Thus, the treated used glass may contain per ton not more than 20 g of opaque foreign particles or bodies such as ceramics, porcelain or stones and not more than 5 g of non-ferrous metals. These high degrees of purity are required because presently more than 95 per cent of used glass is added to a melt for producing new glass. These high degrees of purity have to be guaranteed by the processors of used glass and have to be proved by samples of the treated used glass. As the sampling is made at regular intervals during the treatment and as large sample amounts are required due to the low amount of permissible impurities, in particular ceramics, stones, porcelain and non-ferrous metals, the analysis of the treated used glass is very complex and expensive. This is further exacerbated by the fact that the samples presently have to be evaluated manually.

In the conventional method, the foreign materials, which are sorted into fractions respectively comprised of non-ferrous metals and opaque foreign materials such as ceramics, porcelain, stones or the like, are removed from each sample quantity, thereafter weighed and their weight is related to that of the sample quantity.

SUMMARY OF THE INVENTION

It is an object of the present invention to provide a process which enables a simple analysis of a sample quantity of treated used glass to be made and which is also suitable for being carried out in an automated manner.

It is a further object of the present invention to provide an apparatus for carrying out the method in accordance with the invention.

In a method of the kind as mentioned above, this and other objects are accomplished according to this invention by piling the sample quantity of the treated used glass in a layer, allowing the treated used glass of the layer to trickle over a free-falling path, blowing out foreign bodies comprised of non-ferrous metals and of opaque foreign materials, and separately collecting the foreign bodies of non-ferrous metals and the opaque foreign materials in separate containers.

The blowing out of foreign bodies from a cascading stream of impure glass particles in a free-falling path is known in the treatment of used glass, but there is in this process no separation according to the type of impurity and there is also no weighing of the individual fractions.

By means of the proposed measures, an adaptation of a proven method for analyzing purposes is achieved in a simple manner.

To prevent particles of the treated used glass from sticking to one another through a moisture film so that stuck-together particles are blown out together, it is proposed according to a further feature of the invention to dry the sample quantity before it is permitted to cascade over the free-falling path. This increases the separation selectivity in sorting out foreign bodies.

According to a further feature of the invention, it is proposed that the foreign bodies collected from at least one sample in the containers for receiving the foreign bodies of non-ferrous metals or the opaque foreign materials respectively are manually sorted to determine the amount of the glass particles which have been blown out too, and that from the ratio of glass particles to foreign bodies a correction factor is calculated which is taken into account in determining the proportion of the respective foreign bodies in the treated used glass. This results in a considerable increase in the preciseness of the analysis with relatively little effort, as in raw materials which remain substantially unchanged the correction factor only has to be determined at larger intervals or after a larger number of samples and, therefore, despite the high precision of the analysis, only little manual work is required.

According to a further feature of the invention, it is proposed that particles of less than a predefined size are screened out before the free-falling path and the proportion of the foreign bodies sorted out is related to the remaining sample quantity. This facilitates the purposeful blowing out of the registered foreign bodies.

The apparatus of the present invention comprises a feed device for a stream of treated used glass, a movable sample collector insertable into the stream of treated used glass by movement towards the feed device to collect a sample, a vibrating conveyor downstream of the feed device for receiving the sample of the treated used glass and conveying it in a layer, a chute downstream of the vibrating conveyor and receiving the layer of the treated used glass, the chute defining a free-falling path for the treated used glass sample, sensors for detecting non-ferrous particles and opaque particles arranged along the chute and extending in two rows, the sensors being spaced in the falling direction from one another transversely to the falling path, blower nozzles succeeding the sensors in the falling direction and controlled by the sensors to blow out the sensed non-ferrous and opaque particles to leave pure glass in the free-falling path, and different collecting containers arranged respectively to receive the blown-out non-ferrous particles, the blown-out opaque particles and the pure glass.

This provides a very simple arrangement for a separate registration of opaque particles and particles made of non-ferrous metal by separate rows of sensors, which particles can be separated from the sample of the already treated glass by means of blower nozzles also arranged in two rows. In this manner, it is possible to determine the proportions of impurities according to their type.

According to a further feature of the invention, the apparatus comprises weighing devices for the pure glass container and the containers for the non-ferrous metal particles and the particles of opaque foreign materials. This enables the evaluation to be substantially automated.

According to a further feature of the invention, the vibrating conveyor can be supplied with hot air. This ensures a secure evacuation of the moisture from the sample, thus preventing particles from adhering to one another and thus allowing the individual particles of the sample to trickle separately down the free-falling path. In this way, it is possible that the individual foreign bodies can be blown out substantially singularly without allowing a substantial number of glass particles to be blown out too.

The chute may be provided with a screen for separating particles which fall below a certain dimension. This prevents an undesirable pollution of the environment with fine glass dust, as is otherwise the case in the blowing out of foreign bodies.

BRIEF DESCRIPTION OF THE DRAWING

The above and other objects, advantages and features of the present invention will become more apparent from the following detailed description of a now preferred embodiment thereof, taken into conjunction with the accompanying, somewhat schematic and fragmentary drawing, wherein.

DETAILED DESCRIPTION OF A PREFERRED EMBODIMENT

Figure 1:
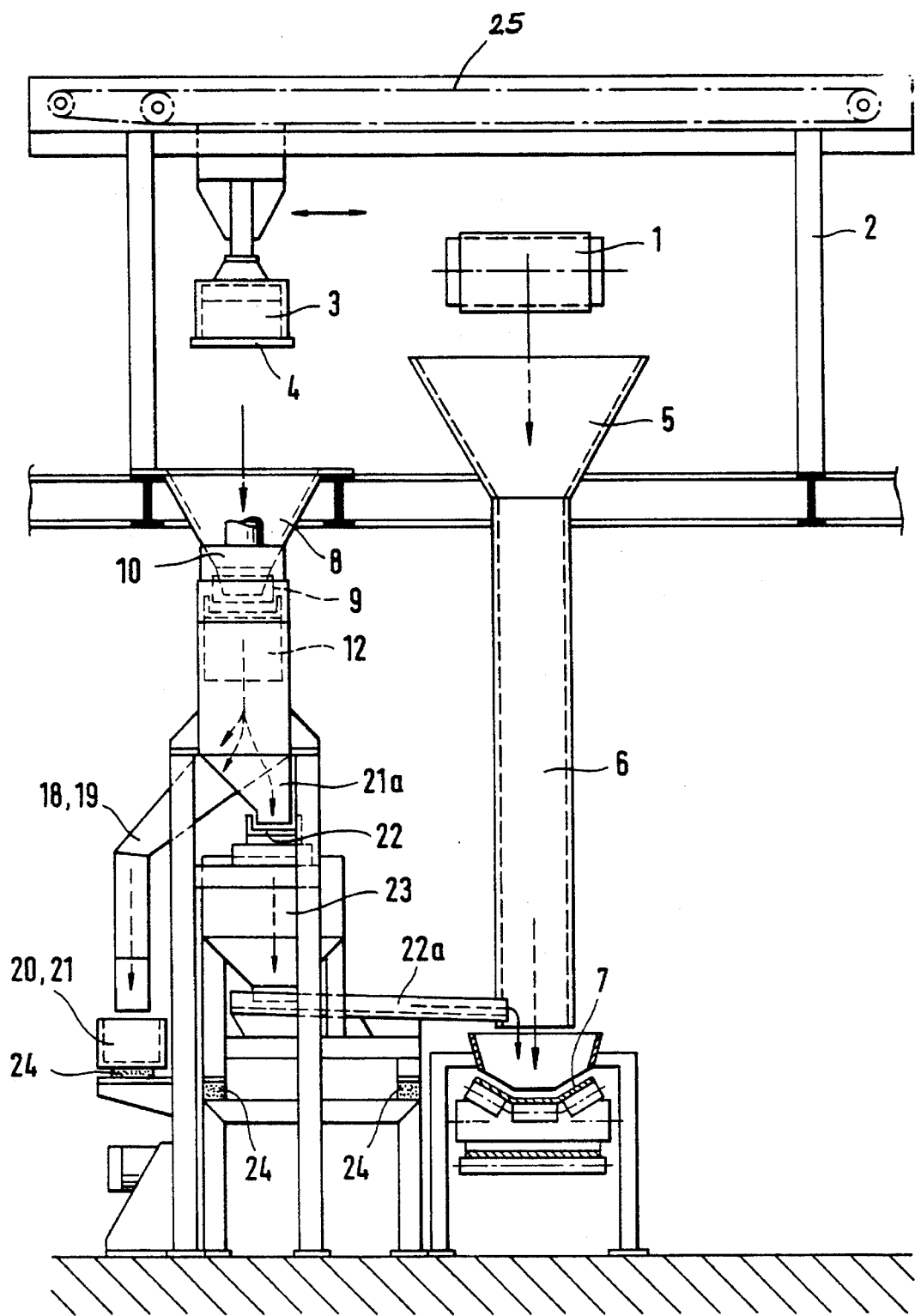
FIG. 1 is a front view of an apparatus according to this invention.
Figure 2:
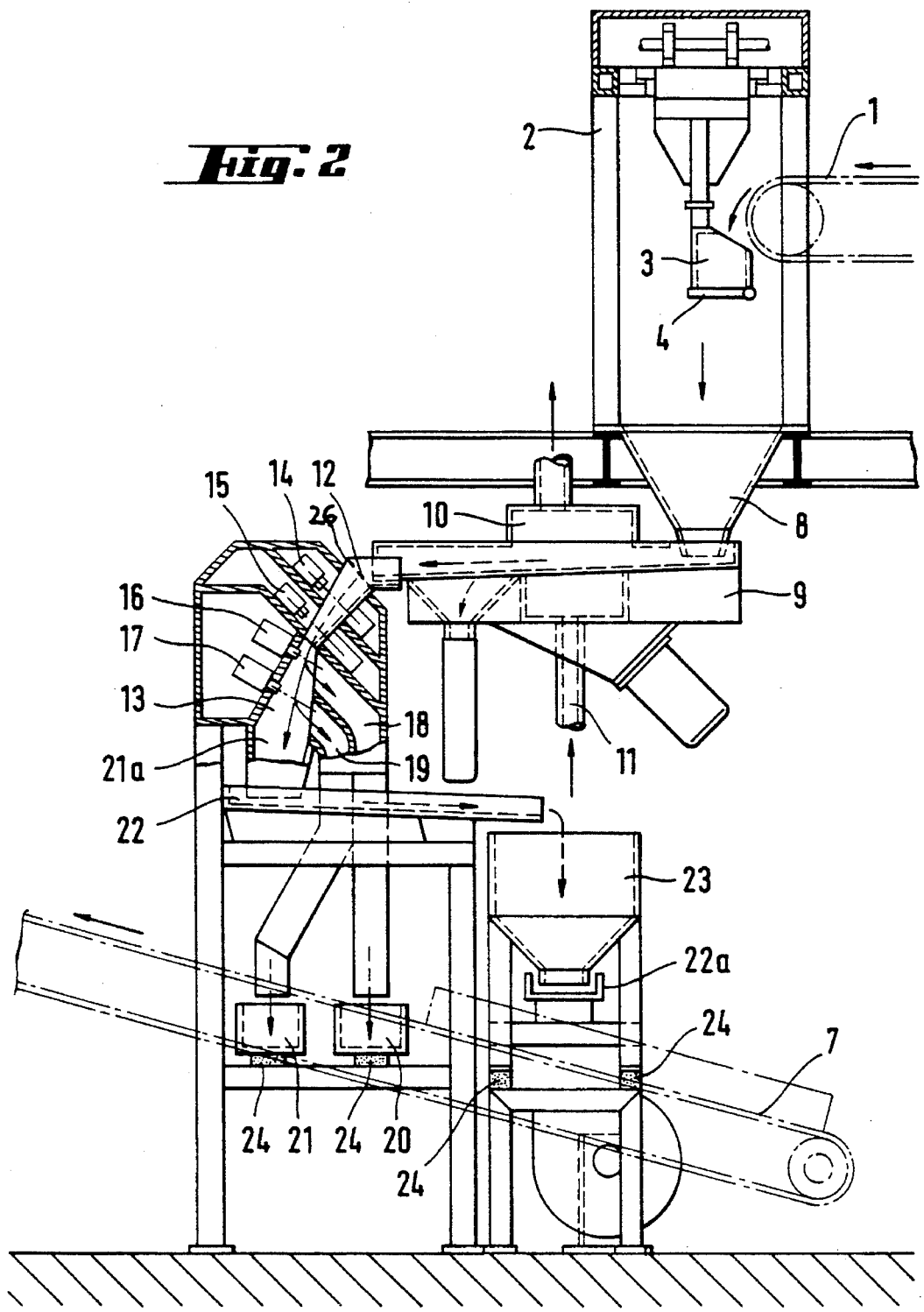
FIG. 2 is a side view of the apparatus.

Frame 2 is arranged at a discharge end of a belt conveyor 1 feeding the treated used glass. The frame extends transversely to the conveying direction of feed belt conveyor 1, and sample collector 3 is movable in the frame transversely to the belt conveyor 1. Sample collector 3 has a downwardly pivotal floor 4 which operates like a trap door and allows the discharge of material from sample collector 3.

Funnel 5 is arranged at the discharge end of belt conveyor 1 and is connected to a standpipe 6 which leads to a further conveyor 7 which supplies the used glass to devices for carrying out further production steps. A further collecting funnel 8 is mounted on support frame 2 in addition to funnel 5, and is used for receiving the sample quantity which was taken and supplied by sample collector 3. This is done by transversely moving the sample collector to the discharge end of belt conveyor 1 to receive a sample quantity of the conveyed treated used glass therefrom. After the sample quantity has been received in the sample collector, it is moved out of the way of the discharge end of the belt conveyor so that it may discharge into funnel 5 again.

Sample collector 3 containing the sample quantity is moved transversely to a funnel 8 by chain drive 25, and trap door 4 can be opened to discharge the sample quantity into the funnel. A vibrating conveyor 9 is arranged below funnel 8 and an air discharge conduit 10 is arranged over the upper side of conveyor 9. Vibrating conveyor 9 can be supplied from below with hot air of 150° C., for example, via an inlet conduit 11 at the underside of conveyor 9, which air is used for drying the sample quantity delivered from funnel 8 to conveyor 9.

Vibrating conveyor 9 conveys a layer of the sample quantity of the treated used glass to a chute 12 at a discharge end of conveyor 9, through which it cascades in free-falling path 13. Particles of less than a predefined size are screened out by screen 26 before the sample quantity cascades down free-falling path 13.

Sensors 14, 15 are arranged in two rows along chute 12 and extend over the whole width of the chute. Sensors 14 are designed for detecting non-ferrous metals and sensors 15 for detecting opaque foreign bodies such as ceramics, porcelain, stones or the like. They control blower nozzles 16, 17 which succeed the sensors along path 13 and are supplied with compressed air. The nozzles are opened briefly under control of the sensors so as to deflect the foreign bodies and to remove them from the glass stream. The blower nozzles 16, 17 are arranged in two rows extending over the whole width of the free-falling path 13, with blower nozzles 16 being controlled by sensors 14 and blower nozzles 17 being controlled by sensors 15.

Guide channels 18, 19 face blower nozzles 16, 17 on the side of the free-falling path which is opposite the blower nozzles, and these channels guide the non-ferrous metals to a collecting container 20 and the opaque foreign bodies to a collecting container 21.

The cleaned glass of the sample is supplied by bottom outlet 21a of chute 12 to a vibrating conveyor 22, which conveys it to the pure glass container 23 where it is collected.

The collecting containers 20, 21 and the pure glass container 23 are placed on weighing cells 24 which are connected to a computer which determines the proportion of foreign material in the sample quantity.

After the analysis of the sample, the pure glass is discharged from container 23 to a vibrating trough 22a, which conveys the pure glass to conveyor belt 7. In this manner, the used glass, as the raw material, is supplied to devices for carrying out further production steps.

What is claimed is:

1. A method for determining the purity of treated used glass, which comprises the steps of (a) removing a sample quantity from a stream of the treated used glass still containing foreign bodies of non-ferrous metals and opaque foreign materials such as ceramic, porcelain and stone particles, (b) piling the removed sample quantity in a layer, (c) permitting the layer of the sample quantity to trickle down in a free-falling path, (d) separating and sorting out fractions of the sample quantity in the free-falling path consisting respectively of the non-ferrous metals and opaque foreign materials, (e) blowing the separated and sorted-out fractions out of the free-falling path whereby a substantially pure treated used glass fraction remains in the path, (f) separately collecting the fractions of non-ferrous metals, of opaque foreign materials and of pure treated used glass in separate containers, (g) weighing each collected fraction and determining the proportions of the fractions of non-ferrous metals and of opaque foreign materials in relation to the fraction of pure treated used glass, and (h) manually sorting out any glass particles blown out with the foreign bodies in at least one of the containers wherein the foreign bodies have been collected, calculating a correction factor determined by the ratio of glass particles to foreign bodies, and taking into account said correction factor in determining the proportions of the weight of the fractions of non-ferrous metals and of opaque foreign materials in relation to the weight of the fraction of pure treated used glass.

* * * * *